Jan. 1, 1952 S. DOMILLA Plant Pat. 1,061
ROSE PLANT
Filed Sept. 26, 1950
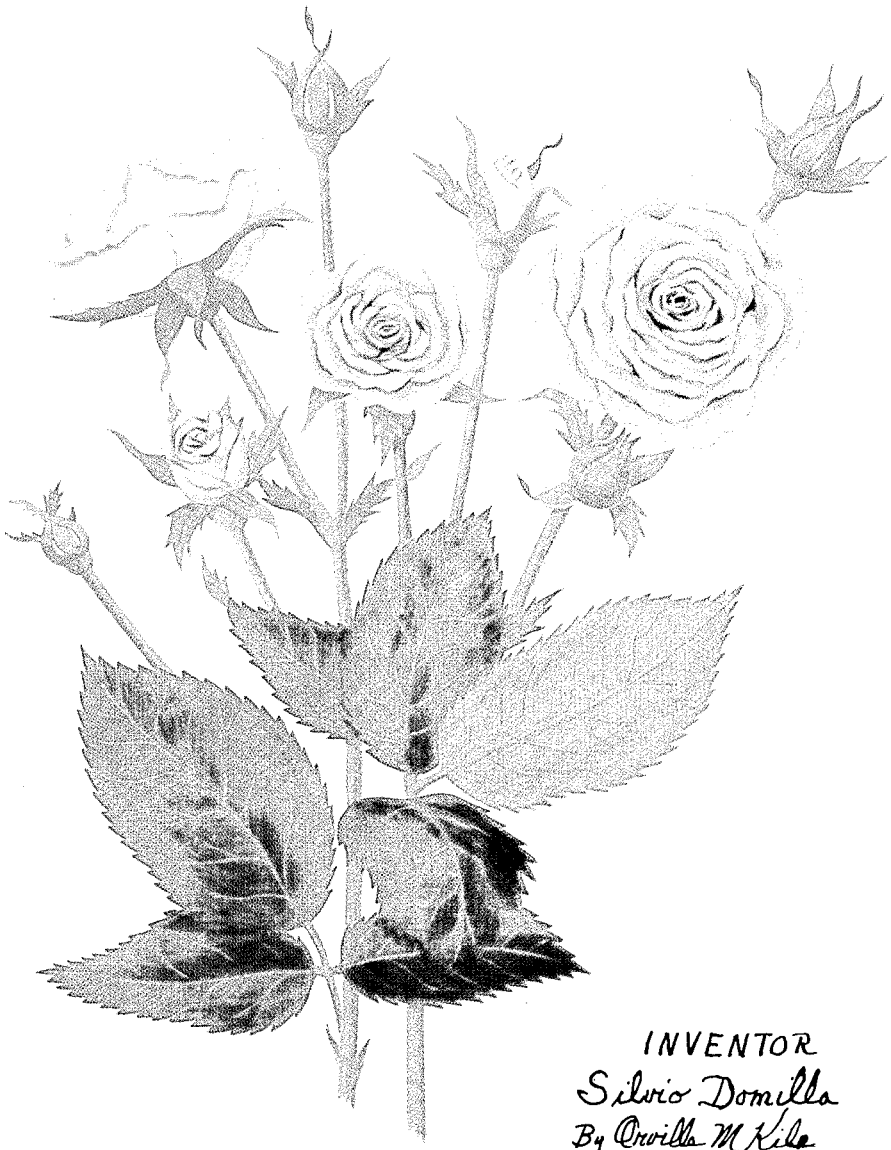
INVENTOR
Silvio Domilla
By Orville M Kile
Plant pat. Agent Patented Jan. 1, 1952

Plant Pat. 1,061

UNITED STATES PATENT OFFICE 1,061

ROSE PLANT

Silvio Domilla, San Lorenzo, Calif., assignor to Twin Nurseries, San Lorenzo, Calif., a partnership Application September 26, 1950, Serial No. 186,790

1 Claim. (Cl. 47—61)

My present invention relates to a new variety of polyantha rose plant and originated as a sport of the variety Garnette (unpatented), in our company gardens near San Francisco. Asexual reproduction of the new variety has been accomplished by me at this same location by budding and its characteristics appear to be permanent.

The accompanying illustration shows three flowers and several buds, together with portions of stems and foliage—all in as nearly the true colors as the artist could make them. However, both the flower and foliage have a great deal more brilliance and lustre than the artist could achieve with the medium used.

Most outstanding among the novel features of this new variety are the bright pink color of its flowers which holds true without becoming blue; its healthy, vigorous and very free growth; and abundant production of flowers which last exceptionally well.

In the following detailed description, color plate numbers refer to Ridgway's Color Standards and Nomenclature.

*The plant*

Growth: Clean and extremely vigorous grower, breaking readily. Form is bushy and it attains a height of from 2 to 4 feet.

Blooming habit:

*Quantity of bloom.*—Very floriferous.

*Borne.*—In clusters of from 3 to 8, with 4 or 5 usually blooming at one time in the larger clusters.

*Season.*—Continuous the year round.

Stems:

*Color.*—Approximately Grass Green (Pl. VI).

*Strength.*—Very strong and upright, branching freely.

*Type.*—Short internodes forming a zigzagged stem.

*Thorns.*—None on upper portion of stems. On lower portion there appear some rather large thorns which are green-tinged, slightly downward-pointing and irregularly placed.

Foliage:

*Leaves.*—Mostly 3 to 5 leaflets. Close to the flower the leaves are single, narrow leaflets and in many cases are very small, sometimes being little more than bracts. Also some of the divided leaves which appear just below the single ones, are three-lobed rather than pinnately divided into three leaflets. However, farther down the stem the leaves are of 3 to 5 leaflets, the terminal leaflet being much larger than the lateral ones.

*Size.*—Below the flower, on the first leaves having 3 to 5 leaflets, the terminal leaflet is 2¼ to 3 inches long by 1½ to 2 inches wide. The first pair of laterals in these leaves are about 1¾ to 2 inches long by 1 to 1½ inches wide and the second pair of terminals, when they occur, are much smaller and measure only a little over an inch long and are proportionately narrow.

*Shape.*—Oval, with acute to acuminate apex. Base sometimes rounded on larger leaflets. Deeply serrated edge, with sharp serrations.

*Texture.*—Leathery. Midrib prominent.

*Rachis.*—Slender; grooved above; smooth on under side except for an occasional small thorn.

*Stipules.*—Clinging and small; points sharp.

*Color.*—Upper surface is dark, lustrous green which is approximately Dark Dull Yellow Green (Pl. XXXII). Under surface approximately same color as stems. New foliage is red or tinged with approximately Indian Red (Pl. XXVIII).

*Disease resistance.*—This variety has been entirely free of mildew at all times and is apparently resistant to all diseases common to roses.

*The flower*

Bud:

*Size.*—Small.

*Form.*—As color first shows, but is rather short but pointed, with sepals meeting above its point thus making it look longer. As the sepals reflex and the bud opens more, it appears flat-topped, and before it finally opens it appears depressed in the center—due partly to the fact that the central petals are shorter and partly to the imbricated arrangement of the petals.

*Sepals.*—Usually rather short, but long enough to "hood" above the bud just before it breaks. Small branched appendages are usually found along sides and there is an occasional foliaceous sepal. Sepals clasp base of bud until open then stand at right angles to stem. Calyx is relatively large and same color as stems.

*Peduncle.*—Short; straight; prickly; slender but strong; same color as stems.

*Opening.*—Bud opens slowly and evenly.

Bloom:

*Size.*—Small to medium, averaging about 1½ to 2 inches in diameter when expanded.

*Form.*—At first the flower has full center and flat top. Later the petals reflex until finally the center opens, revealing the contrasting yellow anthers. In the opening bud and the newly-opened flower the petals often appear to be fluted but in the older flower they appear smooth. The outer petals reflex slightly as the flower gets older.

*Petalage.*—Very double. The number of petals varies greatly, ranging from about 50 to 90.

*Color.*—Very bright, vivid pink or rose color. The exact color is not shown in Ridgway's Color Standards and is difficult to identify, but the nearest is Rose Color (Plate XII). But the newly opened flower is much brighter and more intense in its coloring than this Ridgway plate. The brilliance of the flower is particularly noticeable in artificial light. The reverse side of the petals is somewhat lighter and the white base is more readily visible.

The color lightens somewhat after the flower opens and in three or four days it is pretty close to Rose Color (Pl. XII). After that it often lightens a little more before dying, but it never blues.

*Longevity.*—Exceedingly long-lasting—much above average. As a cut flower it often lasts 10 to 12 days in water and with reasonable care as to temperature.

*Fragrance.*—Abundant and pleasing.

Petals:

*Size.*—Outer petals average about ⅞ inch wide and 1 inch long.

*Shape.*—Obcordate.

*Appearance.*—Silky.

*Texture.*—Soft and rather thin but substantial.

*Arrangement.*—Imbricated.

*Persistence.*—Petals cling well upon opening and hold to the very last.

*Color.*—Bright pink with white base.

Reproductive organs:

*Pistils.*—Many, bunched in center of flowers. Partly enclosed in ovary. *Styles*—slender; white; of uneven lengths. *Stigmas*—creamy white.

*Stamens.*—Fewer than pistils and surrounding them. *Filaments*—irregular lengths and considerably twisted. If straight they would extend about the same height as pistils. *Anthers*—medium size; approximately Snuff Brown (Pl. XXIX). *Pollen*—plentiful; golden yellow.

The variety most like my new variety is its parent, Garnette, but there are a number of differences, the principal ones being as follows:

1. There is a wide difference in flower color.
2. My variety is a 30 to 35 percent freer grower and bloomer.
3. The foliage of my variety is darker and has much less red new foliage.
4. The petals of the flowers of my variety cling better and the flowers have much better keeping quality.

Having thus disclosed my discovery, I claim:

The new and distinct variety of polyantha rose plant, substantially as herein shown and described, characterized particularly by its very strong and healthy growth; its prolific and continuous production of blooms in clusters; its abundant dark green foliage; its very double flowers of bright pink color which holds true without bluing; and the tightly clinging petals and exceptional keeping qualities of its flowers.

SILVIO DOMILLA.

No references cited.